(12) United States Patent
Houvet

(10) Patent No.: US 10,420,594 B2
(45) Date of Patent: Sep. 24, 2019

(54) COAPTATION PLATE COMPRISING A METAL CORE AND A POLYMER OVERMOULD

(71) Applicant: BIOTECH ORTHO, Salon de Provence (FR)

(72) Inventor: Patrick Houvet, Boulogne-Billancourt (FR)

(73) Assignee: TORNIER, Montbonnot-Saint-Martin (FR)

(*) Notice: Subject to any disclaimer, the term of this patent is extended or adjusted under 35 U.S.C. 154(b) by 150 days.

(21) Appl. No.: 15/536,575

(22) PCT Filed: Dec. 17, 2015

(86) PCT No.: PCT/FR2015/053601
§ 371 (c)(1),
(2) Date: Jun. 15, 2017

(87) PCT Pub. No.: WO2016/097636
PCT Pub. Date: Jun. 23, 2016

(65) Prior Publication Data
US 2017/0325861 A1 Nov. 16, 2017

(30) Foreign Application Priority Data
Dec. 19, 2014 (FR) ..................... 14 62982

(51) Int. Cl.
*A61B 17/80* (2006.01)
*A61B 17/00* (2006.01)
*A61B 17/70* (2006.01)

(52) U.S. Cl.
CPC .......... *A61B 17/80* (2013.01); *A61B 17/7059* (2013.01); *A61B 17/809* (2013.01); *A61B 17/8061* (2013.01); *A61B 2017/00526* (2013.01)

(58) Field of Classification Search
CPC .. A61B 17/8061; A61B 17/80; A61B 17/7059
See application file for complete search history.

(56) References Cited

U.S. PATENT DOCUMENTS 4,403,607 A * 9/1983 Woo ................ A61B 17/80
606/70
4,411,027 A * 10/1983 Alexander .......... A61B 17/80
128/DIG. 8

(Continued)

FOREIGN PATENT DOCUMENTS

FR    2 481 920 A1    11/1981
GB    2 405 342 A     3/2005

(Continued)

OTHER PUBLICATIONS

International Search Report issued for PCT/FR2015/053601, dated Mar. 3, 2016, 6 pages.

(Continued)

*Primary Examiner* — Christian A Sevilla
(74) *Attorney, Agent, or Firm* — Duane Morris LLP

(57) ABSTRACT

The present application relates to a coaptation plate comprising a core and an overmold, the core comprising at least one window which is designed to at least partially extend over a fracture which separates a first portion of the osseous tissue from a second, the window being positioned between two openings through which a fastening screw passes, wherein one of said openings lies at least partially within a proximal portion of the core and the other opening lies at least partially within a distal portion of the core, the overmold enclosing the core and forming at least one upper layer and one lower layer on either side of the core, the window defining polymer material links that pass through the core and connect the upper layer and the lower layer, thus ensuring that the overmold is anchored in the core.

17 Claims, 2 Drawing Sheets

(56) References Cited

U.S. PATENT DOCUMENTS

Figure 3:
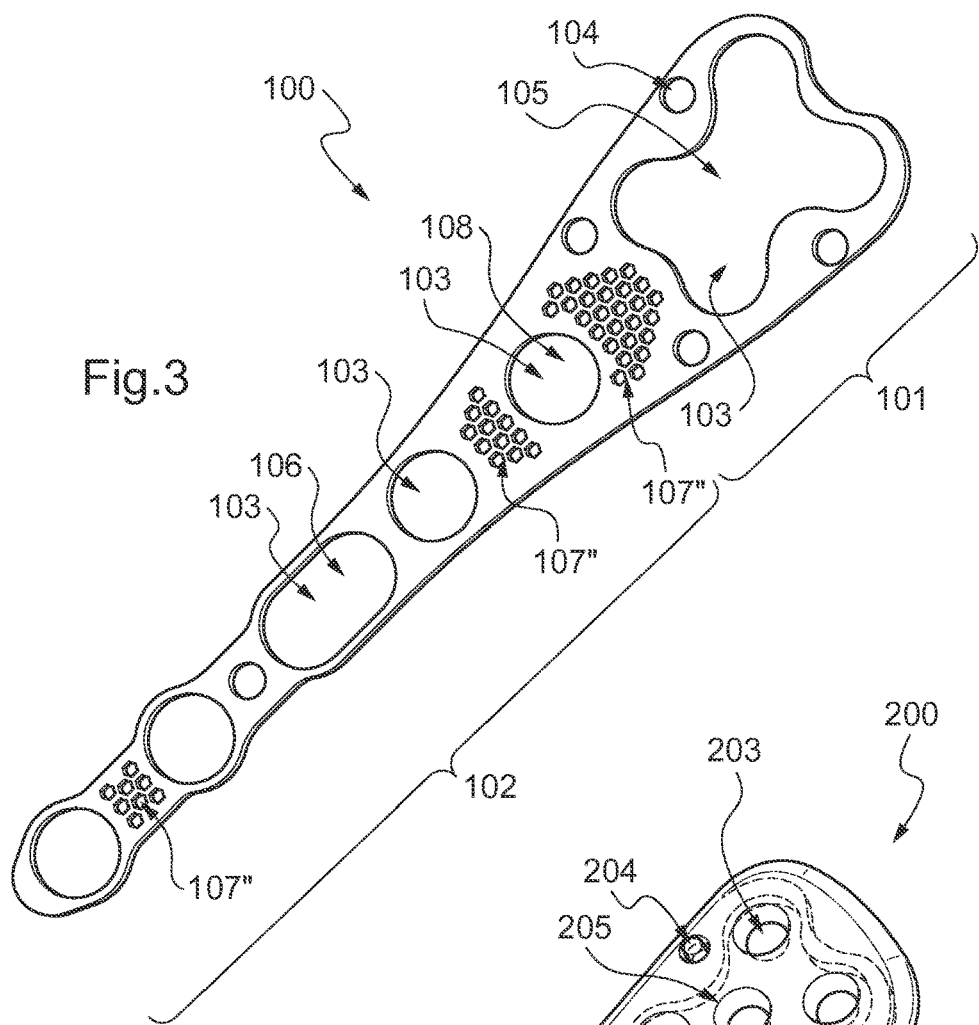

| | | | | |
|---|---|---|---|---|
| 4,743,257 | A * | 5/1988 | Tormala | A61L 31/148 623/23.58 |
| 2010/0131013 | A1 * | 5/2010 | Ralph | A61B 17/80 606/286 |
| 2010/0137996 | A1 * | 6/2010 | Clifford | A61B 17/68 623/23.41 |
| 2013/0178902 | A1 * | 7/2013 | Isch | A61B 17/8085 606/246 |
| 2017/0325861 | A1 * | 11/2017 | Houvet | A61B 17/80 |
| 2018/0289402 | A1 * | 10/2018 | Lueth | A61B 17/1728 |
| 2019/0076174 | A1 * | 3/2019 | Tiongson | A61B 17/808 |

FOREIGN PATENT DOCUMENTS

| | | | |
|---|---|---|---|
| WO | 2007/010671 | A1 | 1/2007 |
| WO | 2014/072983 | A1 | 5/2014 |
| WO | WO-2014072983 | A1 * | 5/2014 ......... A61B 17/7059 |

OTHER PUBLICATIONS

Search Report issued for FR patent application No. 1462982, dated Aug. 7, 2015, 2 pages.

* cited by examiner

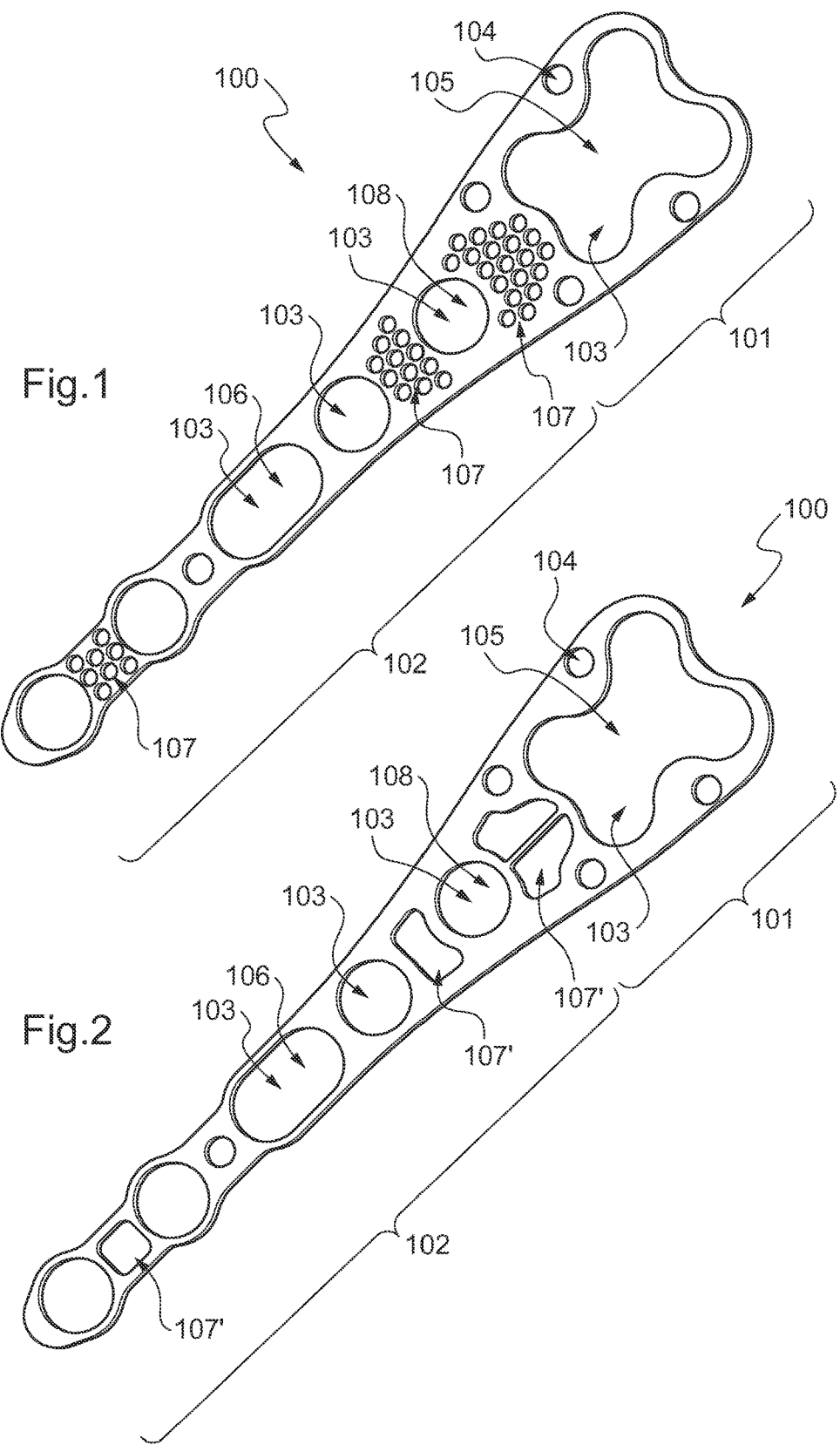

COAPTATION PLATE COMPRISING A METAL CORE AND A POLYMER OVERMOULD

The present application is a United States national stage application under 35 U.S.C. § 371 of international patent application number PCT/FR2015/053601, filed on Dec. 17, 2015, which claims priority to French patent application No. 1462982 filed on Dec. 19, 2014, the entireties of which are incorporated herein by reference.

The present invention relates to a coaptation plate, in particular a coaptation plate including a metal core, for example a proximal humeral plate.

Various options are already known to produce a coaptation plate, in particular for a proximal humeral plate.

For example, a biocompatible proximal humeral plate must provide good stiffening of the proximal part of the humerus after this proximal part has experienced a fracture. The plate must therefore have good flexural rigidity, without generating an excessive overthickness while allowing a wide variety of orientations of the fastening screws fastening this plate to the two parts of the proximal part of the fractured humerus to be secured, all at a reasonable cost and with a minimal weight.

Various solutions have already been proposed, for example a plate made from a single material or a metal plate having PEEK inserts traversed by fastening screws, as in particular described by French patent application FR 2,994,380.

The object of the present invention is to allow better mechanical strength of a coaptation plate, in particular a proximal humeral plate, in combination with a geometry that may be closer to the parts to be put back together, while minimizing mass and without significantly increasing the thickness.

To that end, proposed according to a first aspect of the present invention is a coaptation plate including a metal core and an overmold made from at least one biocompatible polymer material, the core including a proximal part and a distal part, the proximal part being configured to be fastened to a first part of an osseous tissue and the distal part being configured to be fastened to a second part of the osseous tissue, each of the proximal part and the distal part including at least one passage orifice for a fastening screw and a passage orifice for a suture thread, smaller than the passage orifice for the fastening screw. The core further includes at least one window configured to extend over at least part of a fracture separating the first part of the osseous tissue and the second part of the osseous tissue, the window being positioned between two passage orifices of a fastening screw, one of the two fastening screw passage orifices belonging at least partly to the proximal part, the other of the two fastening screw passage orifices belonging at least partially to the distal part. The overmold encloses the core and forms at least an upper layer and a lower layer on either side of the core, the window defining polymer material links traversing the core and connecting the upper layer and the lower layer so as to anchor the overmold in the core.

Here, a window designates a perforation traversing the core, aside from the usual orifices generally dedicated to passages for screws and suture threads.

Furthermore, "passage orifice for a suture thread" here refers to any orifice or hole configured to receive not only a suture thread strictly speaking, for example possibly metal, but also for example a hoop or a pin, in particular a passage orifice for a suture thread in the most distal position of the plate.

Such a core may thus have a smaller thickness than in the known solutions while retaining very good mechanical strength, in particular good flexural strength, as well as the desired radiodensity, i.e., minimal, for such attached pieces. Indeed, the presence of at least one window makes it possible to give the plate better transparency to rays, such as X-rays when an X-ray is required. Such a core is also lighter than a traditional core.

Such a plate thus makes it possible to combine the advantages related to a plate made from several layers.

One alternative to produce a coaptation plate that is transparent to radiography rays is for example to make it entirely from a material transparent to these rays, for example PEEK. However, such a material can be fragile, and if this material breaks, debris is frequently generated, which must be avoided in a human body.

A plate according to the invention thus makes it possible to have good rigidity and robustness owing to the presence of the metal core and at the same time to provide better transparency to radiography rays.

Owing to manufacturing by overmolding, even if the polymer, for example PEEK, breaks, it remains secured to the core, thus limiting the risks of dispersion of any debris.

In parallel, it is also easier to give this core the curves, or warp, necessary to best follow the geometry of the bone part to be treated.

A window may be of any type. It may for example involve cutouts with any shape, juxtaposed holes, or a honeycomb.

According to one interesting example embodiment, the window includes a single opening, or two openings, or a plurality of holes close to one another. The holes of a plurality of holes are for example smaller than the passage orifice for a fastening screw and smaller than the passage orifice for a suture thread.

An arrangement with small holes has the advantage of combining the various aforementioned advantages while allowing a large number of connections between the outer layers of the overmold, i.e., the upper layer and the lower layer. As a result, the outer layers can be connected to one another in a large number of locations, which can be as regularly distributed as desired.

According to one interesting example, the plurality of holes draws a hexagonal network with thin walls forming a honeycomb structure.

A honeycomb for example corresponds to a particular arrangement of small juxtaposed holes, i.e., holes with a hexagonal section and separated from their neighbors by thin walls.

It should be noted that these hexagonal structures evoke a honeycomb structure with the exception that, after overmolding, their cells are filled, the filling material having a connecting role between the layers more than a mechanical reinforcing role.

Furthermore, this is then formed in the plate with the axis of the holes orthogonal to the plate. In other words, the holes of the honeycomb structure traverse a thickness of the plate. Thus, unlike a standard use of a honeycomb, the holes then have a different orientation from a main direction of a compression load.

The presence of a honeycomb makes it possible to give the core, and therefore the plate including it, anisotropic properties best meeting certain expectations under certain circumstances.

According to one example embodiment, the core includes several windows.

The windows are then for example positioned in zones of the core where there are few or no first or second orifices.

In other words, the presence of several windows further makes it possible to best avoid delamination between the different layers of the plate, i.e., the core and the two outer layers of the overmold (i.e., the upper layer and the lower layer), and thus to ensure better robustness of this plate.

For example, the windows represent a surface area comprised between about 20% and about 80% of a surface area of the core, and preferably between about 30% and about 40%.

According to one example embodiment, the proximal part of the core is on average wider than the distal part.

According to one advantageous embodiment, the plate includes a passage orifice for a fastening screw positioned spanning the proximal part and the distal part.

Advantageously, the plate has a mean thickness smaller than or equal to about 3 mm, or about 2.5 mm.

For example, the core has a mean thickness smaller than or equal to about 2 mm, or about 1.5 mm.

Forming the plate with three layers, i.e., the core and the two outer layers of the overmold, can lead to a slight overthickness in some cases, but in return provides very good mechanical strength.

Furthermore, if the core includes the honeycomb, this overthickness of the plate can be offset by the fact that the core can then have a smaller thickness.

According to one example embodiment, the overmold forms, in the location of at least one passage orifice for a fastening screw, or all of the passage orifices for a fastening screw, an insert provided with a through hole, the insert being configured to allow self-tapping of an inner surface of the hole using a screw for fastening the plate on the osseous tissue.

According to another example, the overmold forms a tubular portion in the location of at least one passage orifice for a suture thread.

According to still another example, the overmold occupies an entire volume of at least one window.

The insert(s) are thus secured both to the upper layer and the lower layer, which guarantees better consistency of their positioning.

According to one advantageous embodiment, the overmold forms, in the location of a passage orifice for a fastening screw, at least two inserts each provided with a through hole, each insert being configured to allow self-tapping of an inner surface of the hole using a screw for fastening the plate on the osseous tissue.

According to one particularly interesting example embodiment, the core is made from titanium.

In parallel, any biocompatible and implantable polymer can be considered.

According to one favored example embodiment, the at least one biocompatible polymer is for example a natural polymer or a polymer filled with carbon fibers with the inserts made from a natural polymer to limit the risks of fiber debris during the insertion of the screws.

"Natural polymer" here refers to any raw fiber with no additives.

For example, SRP (self-reinforced polyphenylene), PPSU (polyphenylsulfone), PSU (polysulfone) or PEKK (polyether ketone ketone), which is part of the PAEK family, are natural polymers within the meaning of the present application and are of interest.

According to another interesting example, at least one of the biocompatible polymer materials is a semicrystalline thermoplastic.

For example, the polymers in the PAEK family are particularly convenient and perform well in the context of the present invention, and preferably PEEK, which belongs to this family.

Indeed, PAEKs in themselves generally have a mechanical strength that may be insufficient to allow the elimination of a metal core, but their good mechanical properties make it possible to facilitate the orientation of the fastening screws as needed while guaranteeing their maintenance.

In order to manufacture such a core, a laser fusion method has proven particularly convenient and high-performing.

Thus, according to another aspect, also proposed is a method for manufacturing a coaptation plate including all or some of the features previously described, including the following steps:

A step for producing the core by laser fusion, and

An overmolding step including total overmolding of the core by at least one first polymer material.

The laser fusion makes it possible to produce warped shapes that are more difficult to produce otherwise, while next being able to be combined with a plastic fusion molding method. Furthermore, such a method makes it possible to save considerable production time; for example, it makes it possible to obtain approximately twenty plates at the same time in about six hours, whereas in traditional machining, this would require several steps.

According to one particularly interesting example embodiment, the method includes an additional overmolding step including at least partial overmolding of the core in a second polymer material.

The partial overmolding for example consists of forming the inserts.

According to another example, the metal core would be completely overmolded in a first polymer, then completely overmolded in a second polymer. This for example makes it possible to produce a rigidity gradient, for example in an embodiment where the second polymer would be more deformable than the first, i.e., more conformable to the bones, such that it would better adapt to the geometry of the bones, for example.

Figure 4:
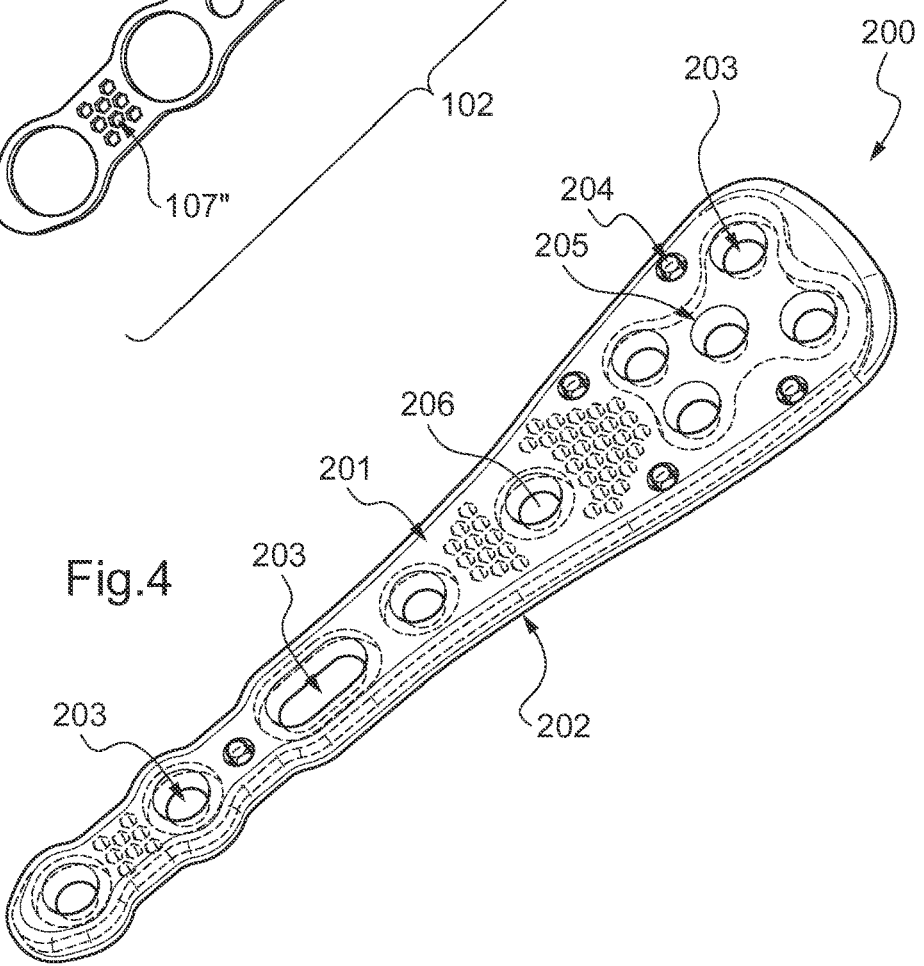

The invention according to one example embodiment will be well understood, and its advantages will better appear, upon reading the following detailed description, provided for information and non-limitingly, in reference to the appended drawings, in which:

FIG. 1 shows a core for a proximal humeral plate according to a first example embodiment of the present invention, FIG. 2 shows a core for a proximal humeral plate according to a second example embodiment of the present invention, FIG. 3 shows a core for a proximal humeral plate according to a third example embodiment of the present invention, and FIG. 4 shows a proximal humeral plate according to one example embodiment of the present invention including the core of FIG. 1.

The identical elements shown in the aforementioned FIGS. are identified using identical numerical references.

In the present description, the expression "underside" designates the face intended to be placed across from the bone fragments for which the coaptation is desired.

In illustration of FIGS. 1 to 4, the under side of the core or the plate is the hidden face. In other words, it is considered here that the face of the cores visible in FIGS. 1 to 3 and the face of the plate visible in 4 are the faces opposite their respective undersides.

The present description here refers to a proximal humeral plate, as an illustration.

The plate includes a core 100 shown individually in FIGS. 1, 2 and 3.

The core 100 is for example made from titanium and using a laser fusion method.

It is considered here that the core includes a proximal part 101 and a distal part 102.

Here, the proximal part 101 is substantially wider, on average, than the distal part 102.

The same is true for the plate including the core 100, like that shown in FIG. 4.

In the present case, the proximal part is intended to be fastened to a proximal part of the humerus, while the distal part is intended to be fastened to the distal part of the humerus; the proximal part and the distal part of the humerus then being separated from one another by the fracture to be treated.

The core 100 primarily includes fastening screw passage orifices 103 and suture thread passage orifices 104.

The fastening screw passage orifices 103 here are holes with a larger diameter, compared to the suture thread passage orifices 104, which have a smaller diameter.

In the present example embodiment, the core includes six fastening screw passage orifices 103, including one in the proximal part 100 one of the core 100, four in the distal part 102 of the core 100, and here, one (identified by numerical reference 108) spanning the proximal part 101 and the distal part 102.

The fastening screw passage orifice of the proximal part 101, identified by numerical reference 105, here positioned at a free end of the proximal part 101 (also called proximal end), is substantially in the shape of a cross. This orifice 105 is thus configured to include up to five inserts 205 for a fastening screw in the overmold 200, as shown in FIG. 4.

The other five aforementioned fastening screw passage orifices 103 are positioned between the orifice 105 and a free end of the distal part 102 (also called distal end).

These other five fastening screw passage orifices 103 are substantially positioned along a median line of the core 100, i.e., along a line going from the distal end to the proximal end.

Furthermore, the orifice situated at the middle of the five orifices, designated by numerical reference 106, is oblong, while the other four orifices are round.

This orifice 106 is thus configured to form a larger fastening screw insert 203, in the overmold 200, as shown in FIG. 4.

Such an orifice makes it possible to fasten the plate to one of the two parts of the bone in a locked manner and makes it easier to bring the second part closer.

Here, there are five suture thread passage orifices 104, four of which are positioned in the proximal part 101 and only one of which is positioned in the distal part 102.

In general, when a proximal humeral plate is positioned on an osseous tissue, the suture threads are primarily necessary at the proximal part of the humerus. Consequently, it is of interest for several suture thread passage orifices 104 to be positioned in a proximal part of the plate, and therefore in the proximal part 101 of the core 100.

Thus, here for example, the suture thread passage orifices 104 positioned in the proximal part 101 are preferably configured to receive a suture thread strictly speaking, for example a metal suture thread, or a hoop; and the suture thread passage orifice 104 positioned in the distal part 102, in particular if it is positioned toward a distal end of this part, is configured preferably to receive a pin, or otherwise a suture thread, for example of the same type mentioned above.

Two suture thread passage orifices are for example positioned here on either side of the core, i.e., on each side and substantially opposite one another, so as to contribute to a proper application of the plate against a bone to be treated.

Thus here, the core includes two pairs of suture thread passage orifices 104 with, in each pair, an orifice positioned toward a right edge of the core and an orifice positioned toward a left edge of the core, as illustrated in FIG. 1. In this way, the four suture thread passage orifices 104 appear substantially in the four corners of a trapezoid in the proximal part 101.

Furthermore, a first of the two pairs of suture thread passage orifices 104 surrounds the orifice 105. Additionally, as shown in FIG. 4, the orifice 105 and the two pairs of suture thread passage orifices 104 are positioned such that at least two of the inserts 205 formed in the orifice 105 are thus situated between the four suture thread passage orifices 104 forming the two aforementioned pairs.

The fifth suture thread passage orifice 104, positioned in the distal part 102, then contributes to better orientation stability of the plate when the latter is positioned on the bone to be treated. Here, it is positioned between the orifice 106 configured to form a larger insert 203 and the distal end of the core, and in particular between the orifice 106 and an adjacent fastening screw passage orifice 103.

The core 100 here further includes two windows 107 positioned between two adjacent fastening screw passage orifices 103, 105, 106, 108, and here in particular on either side of the orifice 108 situated spanning the distal part and the proximal part. The windows 107 are thus configured to extend on either side of the fracture separating the first part of the osseous tissue and the second part of the osseous tissue to be treated. It is thus easier to observe the fracture and its evolution, for example in radiography.

The core 100 here further includes a third window 107 separate from those previously mentioned.

The windows make it possible to have the most hollow core possible while guaranteeing the rigidity of the core, thus making the bone easier to view.

Furthermore, the presence of windows makes it possible to produce more potential connection points between an upper layer 201 and a lower layer 202 that are formed by an overmold of the core, which contributes greatly to avoiding delamination of the different layers.

To that end, it will for example be noted that the windows 107 are formed as close as possible to the fastening screw passage orifices 103.

It is in fact important that once the core 100 is overmolded, the inserts 203 intended to receive a fastening screw have the most stable position possible to facilitate subsequent precise positioning of the fastening screws in the osseous tissue.

As previously mentioned, the first window 107 thus for example extends in the proximal part 101 of the core 100, lengthwise between the orifice 105 configured to receive several inserts 205 and the fastening screw passage orifice 108 directly adjacent thereto, and widthwise over the entire plate, and here between a pair of suture thread passage orifices 104.

The second window 107 here extends lengthwise between the orifice 108 and a fastening screw passage orifice 103 directly adjacent thereto, and widthwise substantially over the width of the core 100.

The third window 107 here in the distal part 102 of the core 100, lengthwise between two fastening screw passage orifices 103 and widthwise substantially over the width of the core 100.

The windows 107 are for example distributed in the core so as to represent, together, between about 20% and about 80% of a surface area of the core 100, for example seen from a face like that shown in FIG. 1.

In the example embodiment of FIG. 1, each window is made up of a plurality of small holes, here for example substantially circular. This thus makes it possible to create a multitude of anchoring points for the overmold while ensuring the desired radio-transparency and reinforcing the mechanical rigidity of the core.

Each hole for example has a diameter comprised between about 0.5 mm and about 10 mm, for example between about 1 mm and 4 mm. The size of the holes is preferably adapted to the material used for the overmold, so as to avoid potential diffusion problems.

Furthermore, two adjacent holes define a wall between them that for example has a thickness comprised between about 100 μm and 5 mm, preferably about 0.5 mm.

The embodiment of FIG. 2 differs in that each window is made up of a single opening, optionally two, as is the case here for the first window situated between the orifice 105 and the orifice 108.

The other elements identical to those of the first embodiment are therefore not described again.

In this embodiment, the first window 107' situated in the proximal part 101 between the orifice 105 and the fastening screw passage orifice 108 directly adjacent thereto, here is substantially lung-shaped.

The second window 107', between the orifice 108 and a fastening screw passage orifice 103 directly adjacent thereto, here has a globally rectangular shape, one side of which follows a curved part of the orifice 108 so as to be able to be as large as possible while preserving good rigidity of the core.

The third window 107', situated in the distal part 102 of the core 100 between two fastening screw passage orifices 103, here is substantially square.

The embodiment of FIG. 3 differs from that of FIG. 1 in that windows 107", situated in the same locations, are formed in a honeycomb.

The presence of the honeycomb thus makes it possible to give the core a smaller thickness while retaining very good mechanical strength, in particular good flexural strength, as well as the desired radiodensity for such attached pieces, in addition to increased lightness. Furthermore, the presence of at least one honeycomb zone makes it possible to give the core, and therefore the plate including it, anisotropic properties best meeting expectations under certain circumstances.

Here, each honeycomb window 107" includes a mesh of holes, the section of which is hexagonal, and particularly a regular hexagon, i.e., all six sides of which have substantially the same length.

Each side of a hexagonal hole for example measures between about 0.5 mm and about 10 mm, for example between about 1 mm and 4 mm. The size of the holes is preferably adapted to the material used for the overmold, so as to avoid potential diffusion problems.

Furthermore, two adjacent holes define a wall between them that for example has a thickness comprised between about 100 μm and 1 mm, preferably about 0.5 mm.

According to another example that is not shown, depending on the arrangement of the fastening screw passage orifices in the core, it is potentially interesting for a window formed from a plurality of small holes, or a honeycomb, to at least partially surround a fastening screw passage orifice.

FIG. 4 shows a plate including the core 100 of FIG. 1 overmolded, here with a polymer, and in particular PEEK.

The description that follows is of course valid in the case where the core is that shown in FIG. 2 or 3.

The overmold is for example made using a plastic injection method.

PAEKs, and here in particular PEEK, are particularly convenient and perform well in the context of the present invention.

Indeed, PAEKs in themselves generally have a mechanical strength that may be insufficient to allow the elimination of a core, but their good mechanical properties make it possible to form inserts facilitating the orientation of the fastening screws as needed while guaranteeing their maintenance.

The plate thus includes an overmold 200 that includes two outer layers: the lower layer 202 across from the underside of the core 100 and the upper layer 201 across from the opposite face.

Aside from the different elements described below, the upper layer 201 and the lower layer 202 are for example connected to one another around the entire perimeter of the core 100.

The plate thus includes three layers in thickness: the upper layer 201, the core 100 and the lower layer 202.

The overmold 200 occupies the volume of each of the windows 107.

In the present example embodiment, the arrangement of the plurality of holes thus has the advantage of combining the various aforementioned advantages while allowing a large number of connections between the outer layers 201 and 202 of the overmold 200. As a result, the outer layers 201, 202 can be connected to one another in a large number of locations, which can be as regularly distributed as desired.

To that end, the windows 107 are therefore advantageously positioned in zones of the core where there may be few or no orifices such as the fastening screw passage orifices 103 or the suture thread passage orifices 104.

Furthermore, the overmold makes it possible to form inserts 203 and suture thread passage tubes 204.

An insert 203 is formed in a fastening screw passage orifice 103.

An insert 203 is provided with a through hole 206 and is configured to allow self-tapping of an inner surface of the hole 206 using a screw for fastening the plate on an osseous tissue.

Each insert 203 is thus secured both to the upper layer 201 and the lower layer 202, which guarantees better consistency of their positioning.

In the present example embodiment, the inserts 203 are made with the overmold assembly, i.e., from a single material following a same overmolding operation, for example.

However, another possible embodiment not shown for example consists of producing the overmold of the core with the exception of the inserts during a first step, and producing the inserts during a second step. Furthermore, in this case, the inserts can be made from a polymer material different from that used during the first step.

The overmold 200 further forms, at the suture thread passage orifice 104, a tubular portion or passage tube 204.

The arrangement of the inserts 203 and tubes 204 is therefore not described in detail here, since it is similar to that of the orifices 103 and 104 previously described.

We will, however, note an exception here for five inserts, more particularly identified as "inserts 205", formed in the orifice 105 previously described. Indeed, in this case, for a single orifice, the orifice 105, five inserts are formed. This makes it possible to have greater freedom to choose the positioning of the inserts during overmolding.

The presence of a larger orifice, the orifice 105, in a wider part of the core, further makes it possible to decrease the mass of the core, increasing its radio-transparency and decreasing its weight.

A plate according to the invention, with three layers, i.e., for example including the core 100 and the two outer layers of the overmold 201 and 202, can lead to a slight overthickness on average, but in return provides very good mechanical strength.

This overthickness is, however, offset by the fact that the core 100, in particular owing to the presence of a honeycomb, can have a smaller thickness, as previously stated.

Thus for example, the plate has a mean thickness smaller than or equal to about 2.5 mm, while the core 100 has a mean thickness of about 1.5 mm.

Of course, the present invention is not limited to the above description or the appended figures: the various features described may advantageously be combined. Their presence in the description does not preclude the possibility of combining them.

The invention claimed is:

1. A coaptation plate, including a metal core and an overmold made from at least one biocompatible polymer material, the core including a proximal part and a distal part, the proximal part being configured to be fastened to a first part of an osseous tissue and the distal part being configured to be fastened to a second part of the osseous tissue, each of the proximal part and the distal part including at least one fastening screw passage orifice for a fastening screw and a suture thread passage orifice for a suture thread, the suture thread passage orifice being smaller than the at least one fastening screw passage orifice,
wherein the core further includes at least one window configured to extend over at least part of a fracture separating the first part of the osseous tissue and the second part of the osseous tissue, the window being positioned between two fastening screw passage orifices, one of the two fastening screw passage orifices belonging at least partly to the proximal part, the other of the two fastening screw passage orifices belonging at least partially to the distal part, and wherein the overmold encloses the core and forms at least an upper layer and a lower layer on either side of the core, the window defining polymer material links traversing the core and connecting the upper layer and the lower layer so as to anchor the overmold in the core.

2. The coaptation plate according to claim 1, wherein the window includes a single opening.

3. The coaptation plate according to claim 1, wherein the window includes two openings.

4. The coaptation plate according to claim 1, wherein the window includes a plurality of holes close to one another, smaller than the fastening screw passage orifice and than the suture thread passage orifice.

5. The coaptation plate according to claim 4, wherein the plurality of holes draws a hexagonal network with thin walls forming a honeycomb structure.

6. The coaptation plate according to claim 1, wherein the core includes several windows and wherein the windows represent a surface area comprised between about 20% and about 80% of a surface area of the core.

7. The coaptation plate according to claim 1, wherein the proximal part is wider on average than the distal part.

8. The coaptation plate according to claim 1, wherein the coaptation plate includes a fastening screw passage orifice positioned spanning the proximal part and the distal part.

9. The coaptation plate according to claim 1, wherein the coaptation plate has a mean thickness that is smaller than or equal to about 3 mm.

10. The coaptation plate according to claim 1, wherein the core has a mean thickness that is smaller than or equal to about 2 mm.

11. The coaptation plate according to claim 1, wherein the overmold forms, at the at least one fastening screw passage orifice, an insert provided with a through hole, the insert being configured to allow self-tapping of an inner surface of the hole using a screw for fastening the plate on the osseous tissue, wherein the overmold forms a tubular portion at the suture thread passage orifice, and wherein the overmold occupies a whole volume of the at least one window.

12. The coaptation plate according to claim 1, wherein the overmold forms, at the at least one fastening screw passage orifice, at least two inserts each provided with a through hole, each insert being configured to allow self-tapping of an inner surface of the hole using a screw for fastening the plate on the osseous tissue.

13. The coaptation plate according to claim 1, wherein the core is made from titanium and wherein the overmold is made from a semicrystalline thermoplastic.

14. The coaptation plate according to claim 6, wherein the surface area of the windows is comprised between 30% and about 40% of the surface area of the core.

15. The coaptation plate according to claim 1, wherein the coaptation plate has a mean thickness that is smaller than or equal to about 2.5 mm.

16. The coaptation plate according to claim 1, wherein the core has a mean thickness that is smaller than or equal to about 1.5 mm.

17. The coaptation plate according to claim 13, wherein the semicrystalline thermoplastic is PEEK.

* * * * *